(12) United States Patent
Lee et al.

(10) Patent No.: US 9,390,495 B2
(45) Date of Patent: Jul. 12, 2016

(54) APPARATUS AND METHOD OF DISPLAYING ULTRASOUND IMAGE

(71) Applicant: SAMSUNG MEDISON CO., LTD., Hongcheon-gun, Gangwon-Do (KR)

(72) Inventors: Dong-hyun Lee, Gangwon-do (KR); Dong-gyu Hyun, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 280 days.

(21) Appl. No.: 13/859,411

(22) Filed: Apr. 9, 2013

(65) Prior Publication Data

US 2013/0293569 A1 Nov. 7, 2013

(30) Foreign Application Priority Data

May 3, 2012 (KR) .................. 10-2012-0047125

(51) Int. Cl.
*G06T 7/00* (2006.01)
*G06T 11/20* (2006.01)
*G01S 15/89* (2006.01)
*G01S 7/52* (2006.01)
*A61B 8/00* (2006.01)
*A61B 8/08* (2006.01)

(52) U.S. Cl.
CPC .............. *G06T 7/0012* (2013.01); *A61B 8/08* (2013.01); *A61B 8/463* (2013.01); *A61B 8/488* (2013.01); *G01S 7/52066* (2013.01); *G01S 15/8984* (2013.01); *G06T 11/206* (2013.01); *A61B 8/0883* (2013.01); *G01S 15/8993* (2013.01)

(58) Field of Classification Search
CPC .... G06T 11/206; A61B 8/463; G01S 7/52074
See application file for complete search history.

(56) References Cited

U.S. PATENT DOCUMENTS

| | | |
|---|---|---|
| 5,170,792 A | 12/1992 | Sturgill et al. |
| 5,390,676 A | 2/1995 | Katakura |
| 5,441,052 A | 8/1995 | Miyajima |
| 5,447,158 A * | 9/1995 | Nakajima et al. ............. 600/455 |
| 5,701,897 A | 12/1997 | Sano |
| 5,855,556 A | 1/1999 | Shirai |
| 5,910,119 A | 6/1999 | Lin |

(Continued)

FOREIGN PATENT DOCUMENTS

| | | | |
|---|---|---|---|
| JP | 5-146438 A | 6/1993 | |
| JP | 6-245933 A | 9/1994 | |

(Continued)

OTHER PUBLICATIONS

Jagmeet P. Singh and Daniel Gras, Biventricular pacing: current trends and future strategies, Sep. 27, 2011, European Heart Journal, Oxford University Press, pp. 1-11.*

(Continued)

*Primary Examiner* — Jeffery A Brier
(74) *Attorney, Agent, or Firm* — McDermott Will & Emery LLP (57) ABSTRACT

A method of displaying an ultrasound image, the method including: transmitting an ultrasonic signal to an object and obtaining vector Doppler data of a tissue included in the object based on a response signal that is reflected from the object; extracting a velocity magnitude of the tissue from the vector Doppler data of the tissue; and mapping the velocity magnitude of the tissue to a color scale and displaying a mapping result.

23 Claims, 8 Drawing Sheets

(56) References Cited

U.S. PATENT DOCUMENTS

| | | |
|---|---|---|
| 2002/0072674 A1* | 6/2002 | Criton et al. ............... 600/454 |
| 2003/0100832 A1 | 5/2003 | Criton et al. |
| 2011/0196237 A1 | 8/2011 | Pelissier et al. |

FOREIGN PATENT DOCUMENTS

| | | | |
|---|---|---|---|
| JP | H06285065 A | * | 10/1994 |
| JP | 11-89837 A | | 4/1999 |
| JP | 2000-201931 A | | 7/2000 |
| JP | 3253409 B2 | | 2/2002 |
| JP | 2006-055266 A | | 3/2006 |
| JP | 2006055266 A | * | 3/2006 |
| WO | 02/45587 A1 | | 6/2002 |
| WO | 2007/107926 A1 | | 9/2007 |

OTHER PUBLICATIONS

Fen-Chiung Lin, I-Chang Hsieh, Cheng-Hung Lee, and Ming-Sien Wen, Introduction of Tissue Doppler Imaging Echocardiography—Based on Pulsed-wave Mode, 2008, Journal of Medical Ultrasound, vol. 16, Issue 3, 2008, pp. 202-209.*

James T. Willerson, Jay N. Cohn, Hein J.J. Wellens, and David R. Holmes, Jr. (Editors), Cardiovascular Medicine, Third Edition, 2007, Chapter 5, Introduction to Echocardiography, Raymond F. Stainback (Author), pp. 93-136.*

Korean Office Action issued in Korean Application No. 10-2012-0047125 dated Apr. 24, 2014, w/English translation.

Korean Office Action with English translation issued in Korean Application No. Kr 10-2012-0047125 mailed Aug. 30, 2013.

Extended European Search Report issued in European Application No. 13159845.0 dated Jul. 23, 2013.

Buckberg et al., "Cardiac Mechanics Revisted: The Relationship of Cardiac Architecture to Ventricular Function", Contemporary Reviews in Cardiovascular Medicine, Circulation Journal of the American Heart Association, Dec. 9, 2008, pp. 2571-2587.

Criton, A. et al., "Real Time Vector Doppler for Tissue Motion," Proceedings, 2002 IEEE Ultrasonics Symposium. Oct. 8-11, 2002. vol. 2; pp. 1529-1534, with Bibliographic data.

Korean Notice of Allowance issued in corresponding Korean Patent Application No. 10-2012-0047125, mailed on Jan. 26, 2015; 7 pages with partial English translation.

Gorcsan III, J., et al., "Echocardiographic Assessment of Myocardial Strain," Journal of the American College of cardiology; 2011; vol. 58; No. 14; pp. 1401-1413; available online: https://content.onlinejacc.org; downloaded on Feb. 24, 2016.

Ojaghi-Haghighi, Zahra et al., "Echocardiographic Assessment of Left Ventricle Torsion by Tissue Doppler and Velocity Vector Imaging," Iranian Journal of Medical Physics; 2014; vol. 11; No. 2 & 3; pp. 276-283.

Voigt, Jens-Uwe, et al. "Definitions for a common standard for 2D speckle tracking echocardiography: consensus Document of the EACVI/ASE/Industry Task Force to standardize deformation imaging," European Heart Journal—Cardiovascular Imaging; 2015; No. 16; pp. 1-11.

* cited by examiner

APPARATUS AND METHOD OF DISPLAYING ULTRASOUND IMAGE

CROSS-REFERENCE TO RELATED PATENT APPLICATION

This application claims the benefit of Korean Patent Application No. 10-2012-0047125, filed on May 3, 2012, in the Korean Intellectual Property Office, the disclosure of which is incorporated herein in its entirety by reference.

BACKGROUND OF THE INVENTION

1. Field of the Invention

The present invention relates to apparatuses and methods of displaying ultrasound images, and more particularly, to an apparatus and method of displaying a synchronization image of a tissue of an object.

2. Description of the Related Art

Ultrasonic devices are essential equipment for observing an internal structure of an organism. An ultrasonic device, which is a non-invasive inspection device, shows structural details, internal tissues, and flow of fluids in a body.

Inside the body, an object which periodically moves, such as the heart, exists and motions of tissues of the object have to be synchronized with each other. To determine whether the motions of the tissues of the object have been synchronized, a synchronization image produced by the ultrasonic device is mainly used.

A synchronization image is an image regarding motions of an object, and by observing the synchronization image, a tissue which is not synchronized with other tissues of the object may be discovered.

SUMMARY OF THE INVENTION

The present invention provides an apparatus and method of displaying ultrasound images, in which exact motion information of tissues of an object is obtained.

The present invention also provides an apparatus and method of displaying ultrasound images, which provide a synchronization image by which an inspector may intuitively determine whether the tissues of the object have been synchronized.

According to an aspect of the present invention, there is provided a method of displaying an ultrasound image, the method including: transmitting an ultrasonic signal to an object and obtaining vector Doppler data of a tissue included in the object based on a response signal that is reflected from the object; extracting a velocity magnitude of the tissue from the vector Doppler data of the tissue; and displaying a mapping result obtained by mapping the velocity magnitude of the tissue to a color scale.

The displaying the mapping result obtained by mapping the velocity magnitude of the tissue to the color scale may include implementing a synchronization image, which indicates whether a motion of the tissue has been synchronized, by mapping the velocity magnitude of the tissue to the color scale.

The displaying the mapping result obtained by mapping the velocity magnitude of the tissue to the color scale may include displaying a mapping result obtained by mapping the velocity magnitude of the tissue to a brightness scale or a chroma scale between a first color and a second color.

The extracting the velocity magnitude of the tissue may include extracting a velocity magnitude of the tissue in a direction selected by a user.

The displaying the mapping result obtained by mapping the velocity magnitude of the tissue to the color scale may include: extracting a velocity direction of the tissue from the vector Doppler data; and mapping the velocity magnitude of the tissue to a first color if the velocity direction includes a first directional component, and mapping the velocity magnitude of the tissue to a second color if the velocity direction of the tissue includes a second directional component that is opposite to the first directional component.

The first directional component may include a direction for when the object expands, and the second directional component may include a direction for when the object contracts.

The method may further include: selecting at least one position on the tissue based on an input of a user; and displaying a velocity magnitude of the at least one position with respect to time as a first graph.

The method may further include displaying the synchronization image on a first area of a display unit of an ultrasound apparatus and displaying the first graph on a second area of the display unit, which is different from the first area.

The method may further include: obtaining a first reference point, which is located inside the object, and a second reference point and at least one point that are located on the tissue of the object; and displaying a color, which is mapped to a velocity magnitude of the at least one point, as a second graph according to an angle between a first straight line, which connects the first reference point and the second reference point, and a second straight line, which connects the first reference point and the at least one point, and time.

The method may further include displaying the synchronization image on a first area of a display unit of an ultrasound apparatus and displaying the second graph on a third area of the display unit, which is different from the first area.

The synchronization image may include a three dimensional image of the heart.

The implementing the synchronization image may include: extracting a velocity direction of a first tissue included in an upper portion of the heart and a velocity direction of a second tissue included in a lower portion of the heart, based on a twist axis of the heart; and mapping a velocity magnitude of the first tissue to a first color if the velocity direction of the first tissue includes a first directional component, and mapping a velocity magnitude of the second tissue to a second color if the velocity direction of the second tissue may include a second directional component that is opposite to the first directional component.

According to another aspect of the present invention, there is provided an apparatus for displaying an ultrasound image, the apparatus including: a probe that transmits an ultrasonic signal to an object and receives a response signal reflected from the object; a data obtaining unit that obtains vector Doppler data of a tissue included in the object based on the received response signal; a data extraction unit that extracts a velocity magnitude of the tissue from the vector Doppler data of the tissue; and a control unit that maps the velocity magnitude of the tissue to a color scale and displays a mapping result.

The control unit may implement a synchronization image, which indicates whether a motion of the tissue has been synchronized, by mapping the velocity magnitude of the tissue to the color scale.

The control unit may map the velocity magnitude of the tissue to a brightness scale or a chroma scale between a first color and a second color and may display a mapping result.

The data extraction unit may extract a velocity magnitude of the tissue in a direction selected by a user.

The data extraction unit may extract a velocity direction of the tissue from the vector Doppler data, and the control unit may map the velocity magnitude of the tissue to a first color if the velocity direction includes a first directional component and may map the velocity magnitude of the tissue to a second color if the velocity direction of the tissue includes a second directional component that is opposite to the first directional component.

The first directional component may include a direction in which the object expands, and the second directional component may include a direction in which the object contracts.

The control unit may select at least one position on the tissue based on an input of a user and may display a velocity magnitude of the at least one position with respect to time as a first graph.

The apparatus may further include a display unit for displaying the synchronization image and the first graph, wherein the control unit may display the synchronization image on a first area of the display unit and may display the first graph on a second area of the display unit, which is different from the first area.

The control unit may obtain a first reference point, which is located inside the object, and a second reference point and at least one point that are located on the tissue of the object, and may display a color, which is mapped to a velocity magnitude of the at least one point, as a second graph according to an angle between a first straight line, which connects the first reference point and the second reference point, and a second straight line, which connects the first reference point and the at least one point, and time.

The apparatus may further include a display unit for displaying the synchronization image and the second graph, wherein the control unit may display the synchronization image on a first area of the display unit and may display the second graph on a third area of the display unit, which is different from the first area.

The synchronization image may include a three dimensional image of the heart.

The data extraction unit may extract a velocity direction of a first tissue included in an upper portion of the heart and a velocity direction of a second tissue included in a lower portion of the heart, based on a twist axis of the heart, the control unit may map a velocity magnitude of the first tissue to a first color if the velocity direction of the first tissue includes a first directional component, and the control unit may map a velocity magnitude of the second tissue to a second color if the velocity direction of the second tissue includes a second directional component that is opposite to the first directional component.

According to another aspect of the present invention, there is provided a computer-readable recording medium having recorded thereon a computer program for executing the method of displaying an ultrasound image.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The merits and characteristics of the present invention and methods for achieving them will be clear with reference to the embodiments described below in detail with the attached drawings. However, the present invention is not limited to the embodiments disclosed below, and the present invention will be implemented in various forms; rather, these embodiments are provided so that this disclosure will be thorough and complete, and will fully convey the concept of the invention to those of ordinary skill in the art. The present invention is only defined by the following claims. Like reference numbers are used to refer to like elements throughout the specification.

The term 'unit' used in the embodiments indicates a software or hardware component, such as a Field Programmable Gate Array (FPGA) or an Application Specific Integrated Circuit (ASIC), and performs a certain role. However, the term 'unit' is not limited to software or hardware. The term 'unit' may be configured to be in an addressable storage medium or to reproduce one or more processors. Thus, for example, the term 'unit' includes components, such as software components, object-oriented software components, class components, and task components, processors, functions, attributes, procedures, sub-routines, program code segments, drivers, firmware, micro-codes, circuits, data, databases, data structures, tables, arrays, and variables. A function provided in components and 'units' may be performed by combining a smaller number of components and 'units' or further separating additional components and 'units' therefrom.

In the embodiments, "vector Doppler data" is a vector that includes a velocity magnitude and a velocity direction, and the "velocity magnitude", which is a scalar, does not include a direction but indicates only a magnitude of a velocity. The "velocity direction" means a direction to which a specific position of a specific object moves at an arbitrary time. In addition, a "tissue", which is one of units constituting a living body, means a group of cells having the same form or function. In addition, a difference between a frequency of an ultrasonic signal transmitted to an object and a frequency of a response signal is referred to as a Doppler frequency, and a signal having the Doppler frequency is referred to as a Doppler signal.

Figure 1:
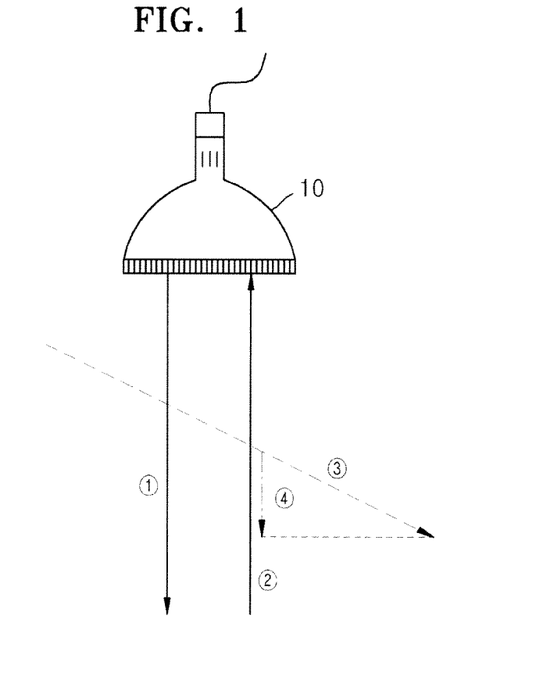
FIG. 1 is a diagram for describing a method of obtaining a velocity magnitude of an object in a general ultrasonic device.

FIG. 1 is a diagram for describing a method of obtaining a velocity magnitude of an object in a general ultrasonic device.

As illustrated in FIG. 1, a probe 10 may transmit an ultrasonic signal to an object (a direction ①) and receive a response signal that is reflected from the object (a direction ②). A Doppler frequency is affected only by a direction ④ which is an orthogonal component, from among movement directions of a blood flow or a tissue, and thus, a general ultrasonic device may obtain only a velocity magnitude of the direction ④ of the blood flow or the tissue. Thus, the general ultrasonic device may not exactly detect a velocity magnitude of a direction ③ of the blood flow or the tissue.

Figure 2:
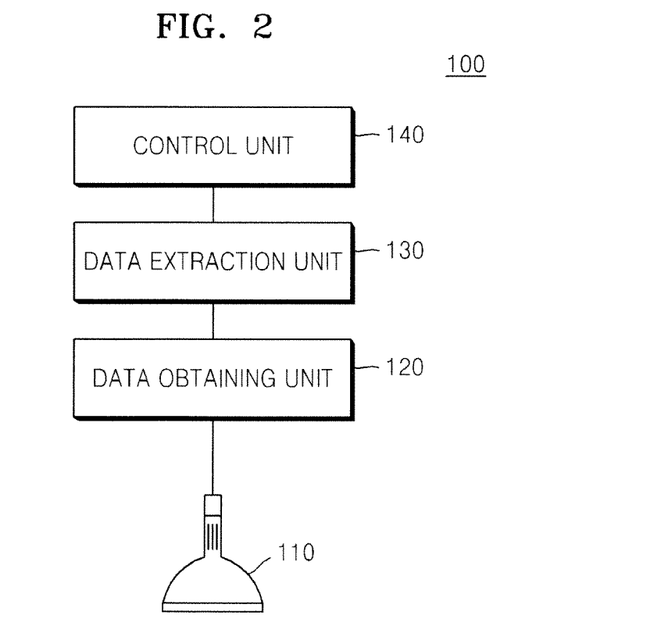
FIG. 2 is a block diagram illustrating a configuration of an apparatus for displaying ultrasound images, according to an embodiment of the present invention.

FIG. 2 is a block diagram illustrating a configuration of an apparatus 100 of displaying ultrasound images (hereinafter, referred to as "an ultrasound image display apparatus"), according to an embodiment of the present invention.

Referring to FIG. 2, the ultrasound image display apparatus 100 may include a probe 110, a data obtaining unit 120, a data extraction unit 130, and a control unit 140. The data obtaining unit 120, the data extraction unit 130, and the control unit 140 may be configured by a microprocessor.

The probe 110 includes a plurality of elements each formed of a piezoelectric device, transmits an ultrasonic signal to an object or a predetermined position of the object, and receives a response signal that is reflected from the object.

The data obtaining unit 120 obtains vector Doppler data of a tissue included in the object based on the received response signal. A method of obtaining vector Doppler data of a tissue will be described below with reference to FIGS. 4 through 6.

The data extraction unit 130 extracts a velocity magnitude of the tissue from the vector Doppler data of the tissue.

The data extraction unit 130 may extract a velocity magnitude of the tissue in a direction selected by a user. If the direction selected by the user is different from a velocity direction of the tissue, a velocity magnitude of the tissue in the direction selected by the user may be extracted by using the velocity magnitude of the tissue and an angle between the direction selected by the user and the velocity direction of the tissue.

In detail, if the velocity magnitude of the tissue is v and the angle between the direction selected by the user and the velocity direction of the tissue is θ, the velocity magnitude v' of the tissue in the direction selected by the user may be v·cos θ.

The control unit 140 maps the velocity magnitude v of the tissue or the velocity magnitude v" of the tissue in the direction selected by the user to a color scale and displays a mapping result. In addition, the control unit 140 may implement a synchronization image, which indicates whether the motion of the tissue has been synchronized, by mapping the velocity magnitude v of the tissue or the velocity magnitude v" of the tissue in the direction selected by the user to the color scale.

In detail, the control unit 140 may map the velocity magnitude v of the tissue to a brightness scale or a chroma scale between a first color and a second color and may display a mapping result. The brightness scale between the first color and the second color means a set of colors having brightness values between a brightness value of the first color and a brightness value of the second color. The chroma scale between the first color and the second color means a set of colors having chroma values between a chroma value of the first color and a chroma value of the second color.

A medical inspector may intuitively determine a non-synchronized tissue based on colors of tissues on the synchronization image. Alternatively, the control unit 140 may implement the synchronization image by mapping only velocity magnitudes of some tissues of the object to a color scale.

Figure 3:
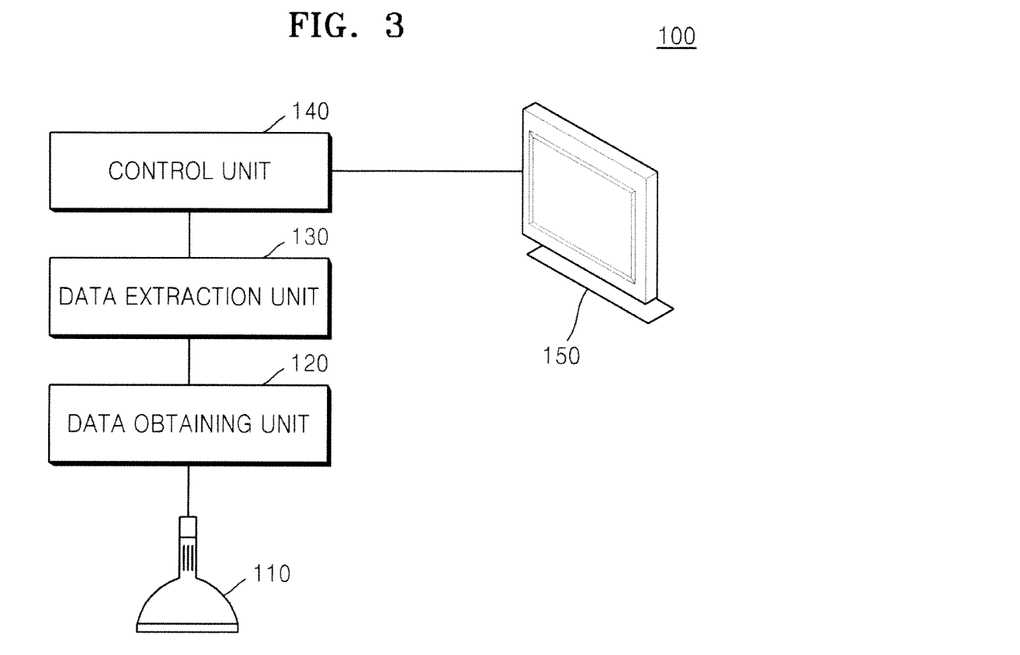
FIG. 3 is a block diagram illustrating a configuration of an apparatus for displaying ultrasound images, according to another embodiment of the present invention.

The ultrasound image display apparatus 100 may further include a display unit 150 as illustrated in FIG. 3.

The display unit 150 displays the synchronization image implemented by the control unit 140 to a user.

Figure 4:
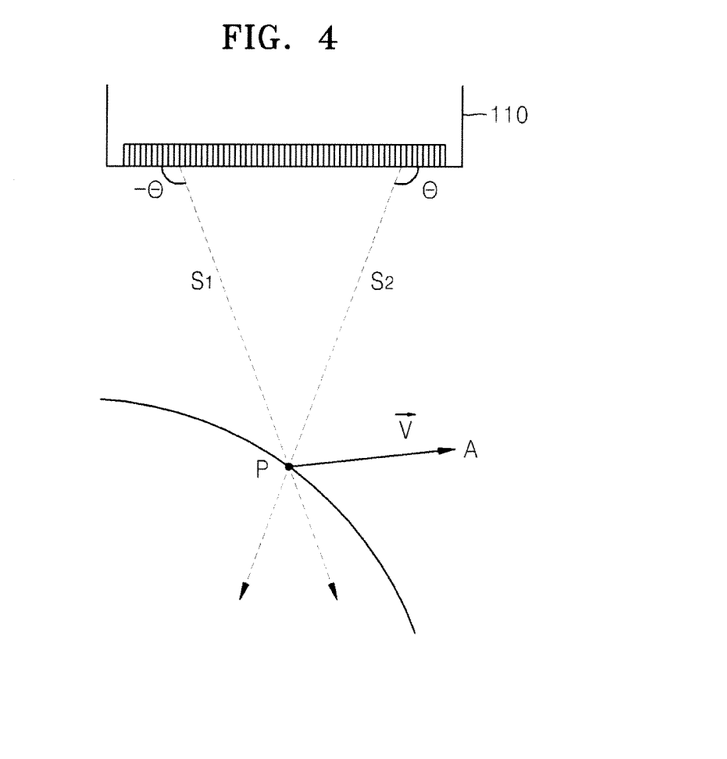
FIG. 4 is a diagram for explaining a method of obtaining vector Doppler data of a tissue, in an apparatus for displaying ultrasound images, according to an embodiment of the present invention.

FIG. 4 is a diagram for explaining a method of obtaining vector Doppler data of a tissue, in the ultrasound image display apparatus 100.

The probe 110 transmits a first ultrasonic signal S1 and a second ultrasonic signal S2 with angles of 180°-θ, and θ to a predetermined position P of an object. The predetermined position P has a velocity magnitude $|\vec{v}|$ and moves in a velocity direction A. Two response signals whose frequencies have been changed by the predetermined position P are received by the probe 110 with reception angles of 180°-θ, and θ.

A method of obtaining vector Doppler data of the predetermined position P by using two response signals having different Doppler frequencies and different reception angles will be obvious to those of ordinary skill in the art pertaining to the vector Doppler, and thus, a detailed description of the method will be omitted here.

In general, the response signals reflected from the predetermined position P include a tissue signal reflected from a tissue and a blood flow signal reflected from a blood flow. Thus, the tissue signal has to be extracted from the response signals to obtain vector Doppler data of the tissue.

Figure 5:
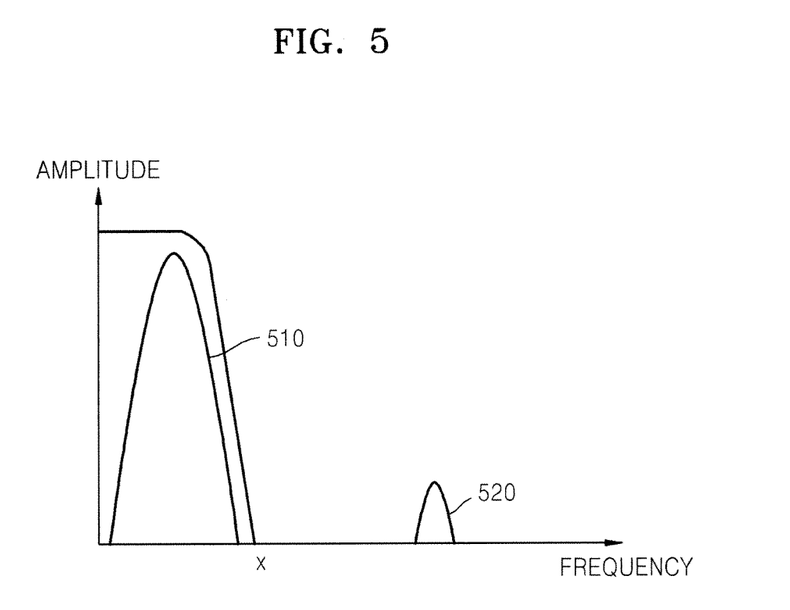
FIGS. 5 and 6 are diagrams for explaining a method of extracting a tissue signal from a response signal, in an apparatus for displaying ultrasound images, according to an embodiment of the present invention.
Figure 6:
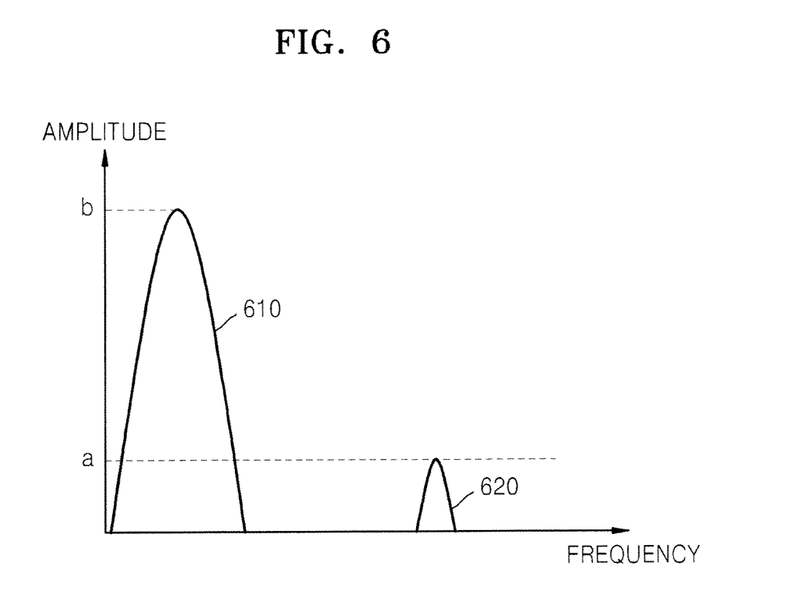

FIGS. 5 and 6 are diagrams for explaining a method of extracting a tissue signal 510 or 610 from a response signal, in the ultrasound image display apparatus 100. FIG. 5 illustrates a blood flow signal 520 and the tissue signal 510 with respect to frequency and the amplitude thereof, and FIG. 6 illustrates a blood flow signal 620 and the tissue signal 610 with respect to frequency and amplitude.

The data obtaining unit 120 extracts the tissue signal 510 or 610 from a response signal reflected from an object. Since the response signal reflected from the object includes the blood flow signal 520 or 620 and the tissue signal 510 or 610, the tissue signal 510 or 610 has to be extracted from the response signal to obtain vector Doppler data of a tissue.

In general, since velocity of blood flow is relatively faster compared to that of tissue, the blood flow signal 520 or 620 is located in a high frequency bandwidth and the tissue signal 510 or 610 is located in a low frequency bandwidth. In addition, since reflectivity of blood flow is very small compared to that of tissue, the power of the tissue signal 510 or 610 is larger than that of the blood flow signal 520 or 620.

The data obtaining unit 120 may extract the tissue signal 510 or 610 from the response signal by using a frequency difference between the blood flow signal 520 or 620 and the tissue signal 510 or 610. That is, the data obtaining unit 120 may extract only the tissue signal 510 or 610 by using a low pass filter having a cutoff frequency x, as illustrated in FIG. 5.

In addition, the data obtaining unit 120 may extract the tissue signal 510 or 610 from the response signal by using a power difference between the blood flow signal 520 or 620 and the tissue signal 510 or 610.

First, the data obtaining unit 120 may calculate a gain value that allows a maximum power of the blood flow signal 520 or 620 to have a predetermined value. In the current embodiment of the present invention, the predetermined value may be a value approximate to "0". In addition, the gain value may be a value that is larger than "0" and smaller than "1".

That is, the data obtaining unit 120 extracts the tissue signal 510 or 610 by applying a gain value, which may make the maximum power of the blood flow signal 520 or 620 be close to "0", to the vector Doppler data. For example, when the maximum power of the blood flow signal 520 or 620 is "a" and the maximum power of the tissue signal 510 or 610 is "b", the data obtaining unit 120 may calculate a gain value "0.0001" that may make the maximum power "a" of the blood flow signal 520 or 620 be approximate to "0". When applying the gain value "0.0001" to the vector Doppler data, a maximum power of the blood flow signal 520 or 620 becomes a×0.0001 that is approximate to "0", and a maximum power of the tissue signal 510 or 610 becomes b×0.0001 that is much larger than "0". Thus, the data obtaining unit 120 may extract the tissue signal 510 or 610 generated by a tissue.

The data obtaining unit 120 may compensate a gain for the tissue signal 510 or 610 extracted by adjusting the gain value. That is, the data obtaining unit 120 compensates a power of the tissue signal 510 or 610 by using a reciprocal of the calculated gain value. For example, since the maximum power of the extracted tissue signal 510 or 610 becomes b×0.0001 when the calculated gain value is "0.0001", the data obtaining unit 120 may make the maximum power of the tissue signal 510 or 610 become "b" by applying the reciprocal "10000 (1/0.0001)" of the calculated gain value to the extracted tissue signal 510 or 610.

Figure 7A:
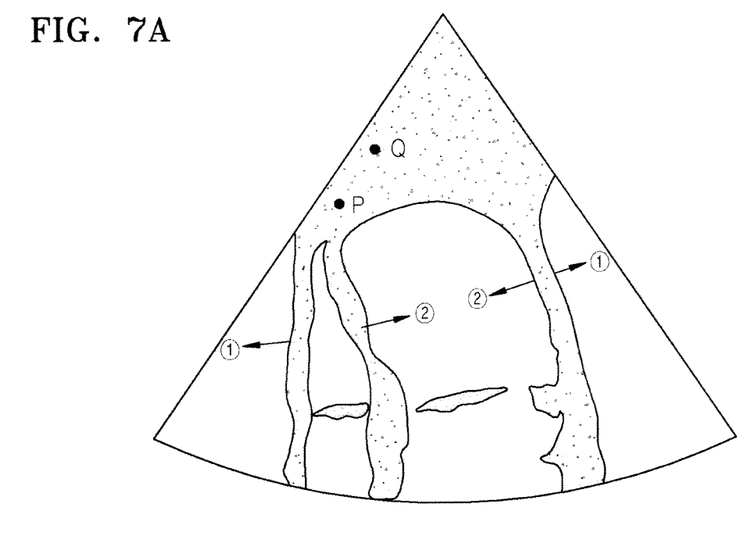
FIG. 7A is a diagram illustrating a synchronization image implemented by an apparatus for displaying ultrasound images, according to an embodiment of the present invention.
Figure 7B:
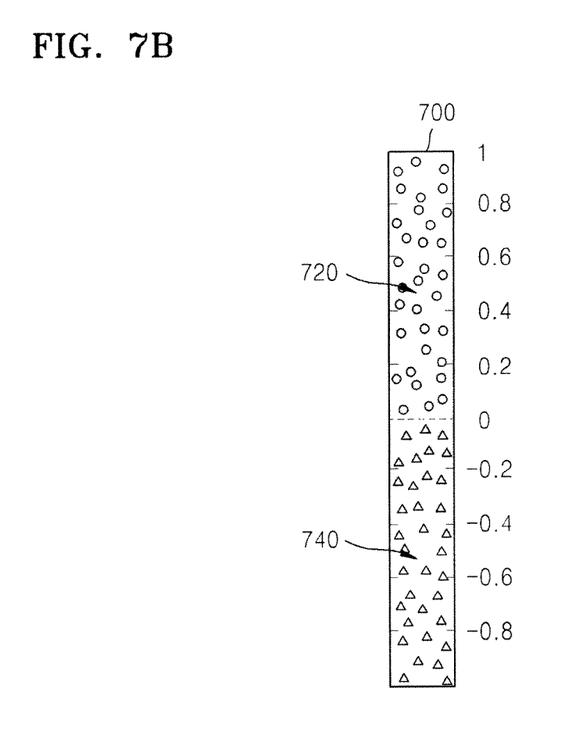
FIG. 7B is a diagram illustrating a color scale that is used for implementing the synchronization image of FIG. 7A.

FIG. 7A is a diagram illustrating a synchronization image implemented by the ultrasound image display apparatus 100 according to the current embodiment of the present invention, and FIG. 7B is a diagram illustrating a color scale that is used for implementing the synchronization image of FIG. 7A.

The data extraction unit 130 may extract a velocity direction of a tissue from vector Doppler data.

The control unit 140 may map a velocity magnitude of the tissue to a first color according to a color scale 700 of FIG. 7B if a velocity direction of the tissue includes a first directional component, and map the velocity magnitude of the tissue to a second color according to the color scale 700 if the velocity direction of the tissue includes a second directional component that is opposite to the first directional component. The first color may be different from the second color.

Referring to FIG. 7B, an upper portion 720 of the color scale 700 may be a color scale which is affiliated with the first color, and a lower portion 740 of the color scale 700 may be a color scale which is affiliated with the second color. Circles in the upper portion 720 indicate the first color, and triangles in the lower portion 740 indicate the second color.

The first directional component may be a direction ① for when an object expands, and the second directional component may be a direction ② for when the object contracts.

In detail, the control unit 140 may map the velocity magnitude of the tissue to an upper portion 720 of the color scale 700 if the velocity direction of the tissue includes the first directional component, and may map the velocity magnitude of the tissue to a lower portion 740 of the color scale 700 if the velocity direction of the tissue includes the second directional component. Accordingly, a medical inspector may easily detect contracting of some tissues when the object expands, and may determine detected tissues as non-synchronized tissues.

The control unit 140 may implement a synchronization image by mapping a velocity magnitude of a tissue in a direction selected by a user to a color scale. In this case, the medical inspector may determine a velocity magnitude of a tissue in a direction desired by the inspector.

Figure 8:
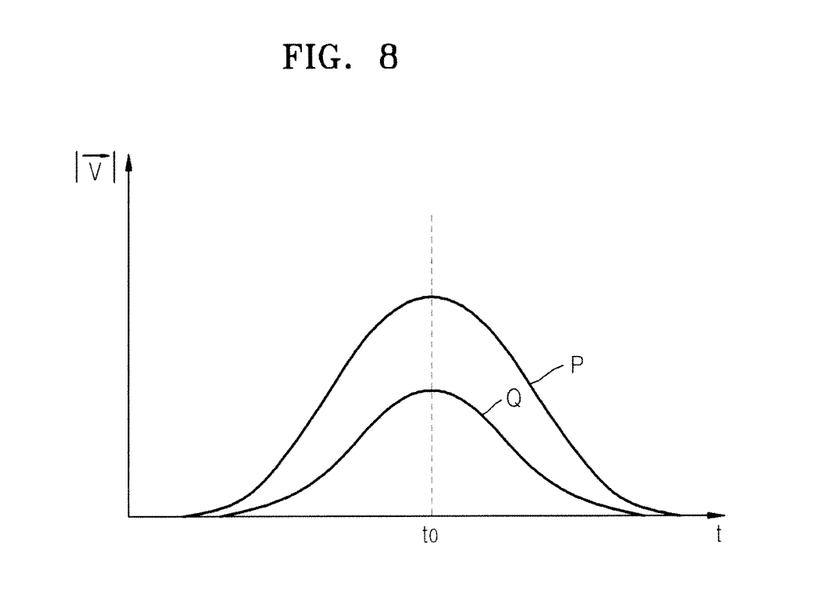
FIG. 8 is a graph illustrating a velocity magnitude of a predetermined position on a tissue with respect to time, in an apparatus for displaying ultrasound images, according to an embodiment of the present invention.

FIG. 8 is a graph illustrating a velocity magnitude of a predetermined position on a tissue with respect to time, in the ultrasound image display apparatus 100 according to the current embodiment of the present invention.

The control unit 140 may select at least one position on a tissue of an object based on an input of a user, and may display a velocity magnitude of the at least one position with respect to time as a graph. When the user selects a point P and a point Q as illustrated in FIG. 7A, a graph such as in FIG. 8 may be displayed on the display unit 150.

The user may determine whether the point P and the point Q have been synchronized, through the graph illustrated in FIG. 8.

The control unit 140 may display the synchronization image illustrated in FIG. 7A on a first area of the display unit 150 and may display the graph illustrated in FIG. 8 on a second area of the display unit 150, and thus, convenience of inspection may be increased.

Figure 9A:
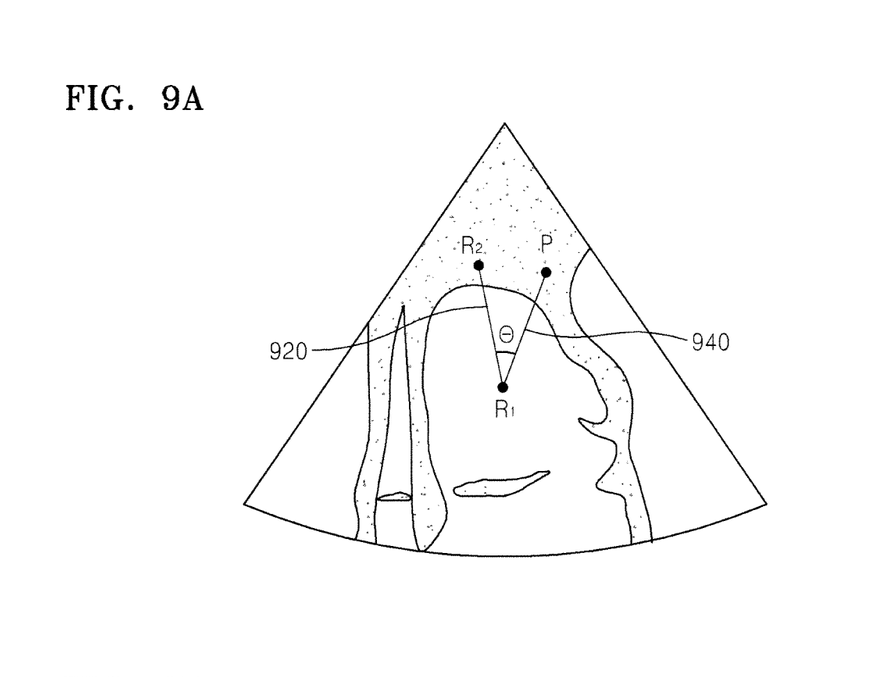
FIG. 9A is a diagram for explaining a method of displaying a velocity magnitude of a tissue as a graph according to an angle and time in an apparatus for displaying ultrasound images, according to an embodiment of the present invention.
Figure 9B:
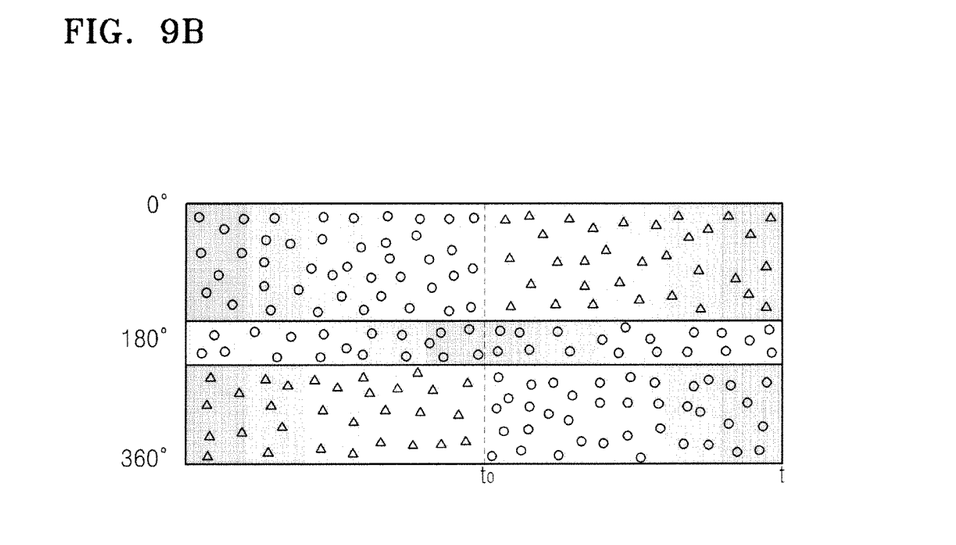
FIG. 9B is a graph illustrating a velocity magnitude of a tissue according to an angle and time, in an apparatus for displaying ultrasound images, according to an embodiment of the present invention.

FIG. 9A is a diagram for explaining a method of displaying a velocity magnitude of a tissue as a graph according to an angle and time, in the ultrasound image display apparatus 100 according to the current embodiment of the present invention, and FIG. 9B is a graph illustrating a velocity magnitude of a tissue according to an angle and time, in the ultrasound image display apparatus 100.

The control unit 140 obtains a first reference point R1 that is located inside an object and a second reference point R2 that is located on a tissue of the object. In addition, the control unit 140 obtains at least one point P that is located on the tissue of the object. The control unit 140 may display a color, which is mapped to a velocity magnitude of the at least one point P, as a graph according to an angle between a first straight line 920, which connects the first reference point R1 and the second reference point R2, and a second straight line 940, which connects the first reference point R1 and the at least one point P, and time. Referring to FIG. 9B, a color of the point P included in the second straight line 940 having an angle difference of 0° through 360° with respect to the first straight line 920 is displayed as a graph according to time. Through the graph illustrated in FIG. 9B, it may be easily determined that a tissue positioned around 180° is a non-synchronized tissue.

The control unit 140 displays the synchronization image illustrated in FIG. 7A on the first area of the display unit 150 and simultaneously displays the graph illustrated in FIG. 9B on a third area of the display unit 150, and thus, convenience of inspection may be increased. In addition, the synchronization image illustrated in FIG. 7A may be displayed on the first area of the display unit 150, the graph of FIG. 8 may be displayed on the second area of the display unit 150, and the graph of FIG. 9B may be displayed on the third area of the display unit 150.

Figure 10:
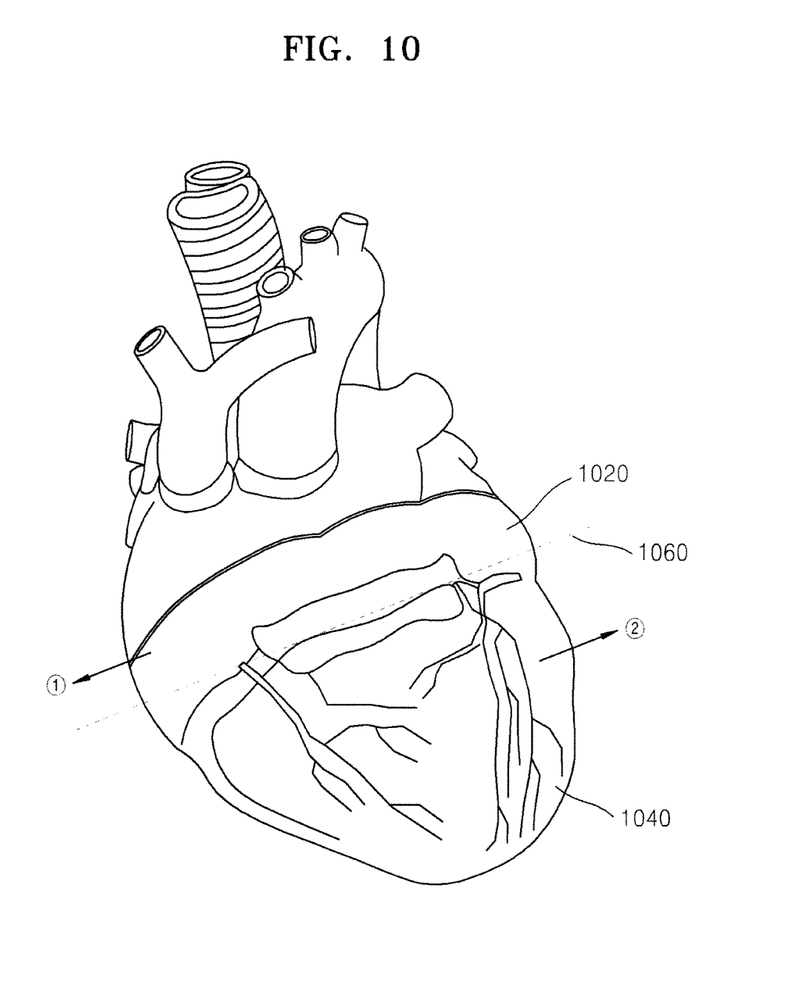
FIG. 10 is a diagram illustrating a three dimensional (3D) synchronization image of the heart, in an apparatus for displaying ultrasound images, according to an embodiment of the present invention.

FIG. 10 is a diagram illustrating a three dimensional (3D) synchronization image of the heart in the ultrasound image display apparatus 100 according to the current embodiment of the present invention.

The control unit 140 may implement an object by using a 3D synchronization image. FIG. 10 illustrates a case where the object is the heart. A twist axis 1060 exists in the center of the heart, and an upper portion 1020 of the heart and a lower portion 1040 of the heart are twisted in opposite directions based on the twist axis.

The data extraction unit 130 extracts a velocity direction of a first tissue included in the upper portion 1020 of the heart and a velocity direction of a second tissue included in the lower portion 1040 of the heart. The control unit 140 may map the velocity magnitude of the first tissue to a first color if the velocity direction of the first tissue includes a first directional component, and may map the velocity magnitude of the second tissue to a second color if the velocity direction of the second tissue includes a second directional component that is opposite to the first directional component.

In FIG. 10, the first directional component may be a direction ①, and the second directional component may be a direction ②. Thus, an inspector may easily determine the extent of twist of the heart.

Figure 11:
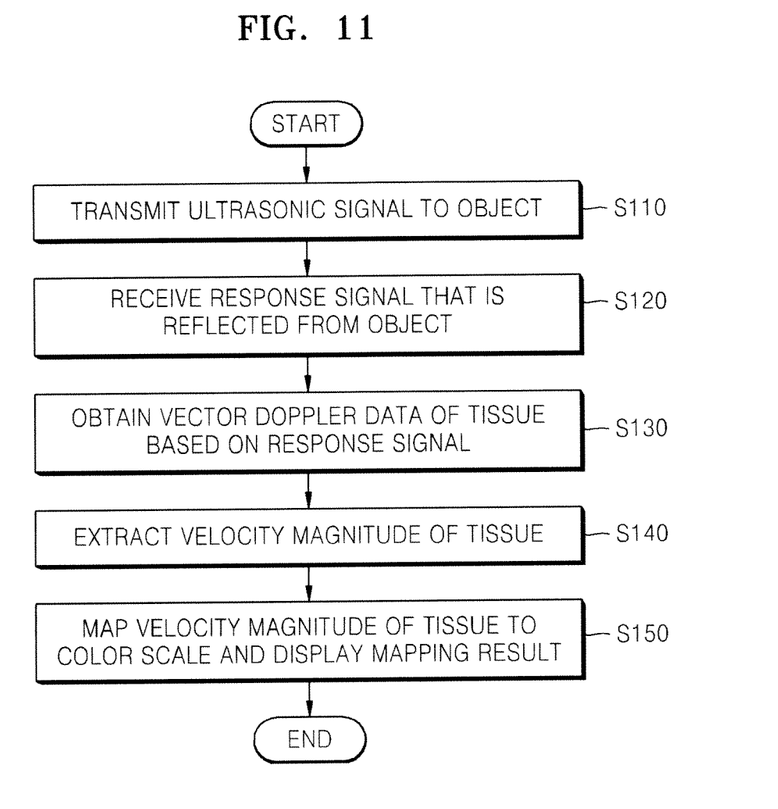
FIG. 11 is a flowchart illustrating a method of displaying ultrasound images, according to an embodiment of the present invention.

FIG. 11 is a flowchart illustrating a method of displaying ultrasound images (hereinafter, referred to as "an ultrasound image display method".), according to an embodiment of the present invention. Referring to FIG. 11, the ultrasound image display method includes operations that are sequentially processed in the ultrasound image display apparatus 100 illustrated in FIGS. 2 and 3. Although omitted below, the content described above with respect to the ultrasound image display apparatus 100 illustrated in FIGS. 2 and 3 may be applied to the ultrasound image display method of FIG. 11.

In operation S110, the ultrasound image display apparatus 100 transmits an ultrasonic signal to an object. The ultrasound image display apparatus 100 may transmit two ultrasonic signals to the object.

In operation S120, the ultrasound image display apparatus 100 receives a response signal that is reflected from the object. The ultrasound image display apparatus 100 may receive two response signals that are reflected from the object.

In operation S130, the ultrasound image display apparatus 100 obtains vector Doppler data of a tissue based on the received response signal. The ultrasound image display apparatus 100 may extract a tissue signal from the received response signal, and may obtain vector Doppler data of a tissue from the tissue signal.

In operation S140, the ultrasound image display apparatus 100 extracts a velocity magnitude of the tissue from the vector Doppler data of the tissue.

In operation S150, the ultrasound image display apparatus 100 maps the velocity magnitude of the tissue to a color scale and displays a mapping result.

The above-described embodiments of the present invention can be implemented as a program which can be executed by a computer, and may be implemented on a general-purpose digital computer which runs the program that may be stored in a computer-readable recording medium.

The computer-readable recording medium may include a magnetic storage medium (e.g., ROMs, floppy disks, hard disks, etc.), optical reading medium (e.g., CD-ROMs, DVDs, etc.), etc.

While this invention has been particularly shown and described with reference to preferred embodiments thereof, it will be understood by those skilled in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. A method of displaying an ultrasound image, the method comprising:
    transmitting an ultrasonic signal to an object and obtaining vector Doppler data of a tissue included in the object based on a response signal that is reflected from the object;
    extracting a first velocity magnitude of the tissue (v) from the vector Doppler data of the tissue;
    receiving an user input for selecting a first direction in the tissue;
    obtaining a second velocity magnitude of the tissue (v') based on the first velocity magnitude of the tissue (v) and a relation between the first direction and a velocity direction of the tissue; and
    displaying a mapping result obtained by mapping the second velocity magnitude of the tissue (v') to a color scale,
    wherein the extracting the first velocity magnitude of the tissue (v) from the vector Doppler data of the tissue comprises extracting the velocity direction of the tissue from the vector Doppler data,
    wherein the displaying the mapping result obtained by mapping the second velocity magnitude of the tissue (v') to the color scale comprises:
    generating a synchronization image by mapping the second velocity magnitude of a first tissue comprising a first directional component to a first color and mapping the second velocity magnitude of a second tissue comprising a second directional component to a second color; and
    displaying the synchronization image.

2. The method of claim 1, wherein the displaying the mapping result obtained by mapping the second velocity magnitude of the tissue (v') to the color scale comprises implementing a synchronization image, which indicates whether a motion of the tissue has been synchronized, by mapping the second velocity magnitude of the tissue (v') to the color scale.

3. The method of claim 1, wherein the displaying the mapping result obtained by mapping the second velocity magnitude of the tissue (v') to the color scale comprises displaying a mapping result obtained by mapping the second velocity magnitude of the tissue (v') to a brightness scale or a chroma scale between the first color and the second color.

4. The method of claim 1, wherein the displaying the mapping result obtained by mapping the second velocity magnitude of the tissue (v') to the color scale comprises:
    mapping the second velocity magnitude of the first tissue to an upper portion of the color scale and mapping the second velocity magnitude of the second tissue to a lower portion of the color scale.

5. The method of claim 4, wherein the first directional component comprises a direction for when the object expands, and the second directional component comprises a direction for when the object contracts.

6. The method of claim 2, further comprising:
    selecting at least one position on the tissue based on an input of a user; and
    displaying a velocity magnitude of the at least one position with respect to time as a first graph.

7. The method of claim 6, further comprising displaying the synchronization image on a first area of a display of an ultrasound apparatus and displaying the first graph on a second area of the display, which is different from the first area.

8. The method of claim 2, further comprising:
obtaining a first reference point, which is located inside the object, and a second reference point and at least one point that are located on the tissue of the object; and
displaying a color, which is mapped to a velocity magnitude of the at least one point, as a second graph according to an angle between a first straight line, which connects the first reference point and the second reference point, and a second straight line, which connects the first reference point and the at least one point, and time.

9. The method of claim 8, further comprising displaying the synchronization image on a first area of a display of an ultrasound apparatus and displaying the second graph on a third area of the display, which is different from the first area.

10. The method of claim 2, wherein the synchronization image comprises a three dimensional image of the heart.

11. The method of claim 10, wherein the implementing the synchronization image comprises:
extracting a velocity direction of a first tissue included in an upper portion of the heart and a velocity direction of a second tissue included in a lower portion of the heart, based on a twist axis of the heart; and
mapping the second velocity magnitude of the first tissue to the first color if the velocity direction of the first tissue comprises a first directional component, and mapping the second velocity magnitude of the second tissue to the second color if the velocity direction of the second tissue comprises a second directional component that is opposite to the first directional component.

12. A non-transitory computer-readable recording medium having recorded thereon a computer program for executing a method of displaying an ultrasound image according to claim 1.

13. An apparatus for displaying an ultrasound image, the apparatus comprising:
a probe for transmitting an ultrasonic signal to an object and receiving a response signal reflected from the object;
a data obtainer for obtaining a vector Doppler data of a tissue included in the object based on the received response signal;
a data extractor for extracting a first velocity magnitude of the tissue (v) and a second velocity magnitude of the tissue (v') from the vector Doppler data of the tissue;
an user interface for receiving an user input selecting a first direction in the tissue;
a controller for mapping the second velocity magnitude of the tissue (v') to a color scale and displaying a mapping result,
wherein the data extractor obtains the second velocity magnitude of the tissue (v') based on the first velocity magnitude of the tissue (v) and a relation between the first direction and a velocity direction of the tissue,
wherein the controller generates a synchronization image by mapping the second velocity magnitude of a first tissue comprising a first directional component to a first color and mapping the second velocity magnitude of a second tissue comprising a second directional component to a second color.

14. The apparatus of claim 13, wherein the controller implements a synchronization image, which indicates whether a motion of the tissue has been synchronized, by mapping the second velocity magnitude of the tissue (v') to the color scale.

15. The apparatus of claim 13, wherein the controller maps the second velocity magnitude of the tissue (v') to a brightness scale or a chroma scale between the first color and the second color and displays a mapping result.

16. The apparatus of claim 13, wherein the controller maps the second velocity magnitude of the first tissue to an upper portion of the color scale and maps the second velocity magnitude of the second tissue to a lower portion of the color scale.

17. The apparatus of claim 16, wherein the first directional component comprises a direction in which the object expands, and the second directional component comprises a direction in which the object contracts.

18. The apparatus of claim 14, wherein the controller selects at least one position on the tissue based on an input of a user and displays a velocity magnitude of the at least one position with respect to time as a first graph.

19. The apparatus of claim 18, further comprising a display for displaying the synchronization image and the first graph, wherein the controller displays the synchronization image on a first area of the display and displays the first graph on a second area of the display, which is different from the first area.

20. The apparatus of claim 14, wherein the controller obtains a first reference point, which is located inside the object, and a second reference point and at least one point that are located on the tissue of the object, and displays a color, which is mapped to a velocity magnitude of the at least one point, as a second graph according to an angle between a first straight line, which connects the first reference point and the second reference point, and a second straight line, which connects the first reference point and the at least one point, and time.

21. The apparatus of claim 20, further comprising a display for displaying the synchronization image and the second graph, wherein the controller displays the synchronization image on a first area of the display and displays the second graph on a third area of the display, which is different from the first area.

22. The apparatus of claim 14, wherein the synchronization image comprises a three dimensional image of the heart.

23. The apparatus of claim 22, wherein the data extractor extracts a velocity direction of a first tissue included in an upper portion of the heart and a velocity direction of a second tissue included in a lower portion of the heart, based on a twist axis of the heart, the controller maps the second velocity magnitude of the first tissue to the first color if the velocity direction of the first tissue comprises a first directional component, and the controller maps the second velocity magnitude of the second tissue to the second color if the velocity direction of the second tissue comprises a second directional component that is opposite to the first directional component.

* * * * *